United States Patent [19]
Etheredge et al.

[11] Patent Number: 5,928,184
[45] Date of Patent: Jul. 27, 1999

[54] MULTI-LAYER ABSORBENT ARTICLE

[75] Inventors: Robert Etheredge, Natick; Marion Scocca, Peabody, both of Mass.

[73] Assignee: Tampax Corporation, White Plains, N.Y.

[21] Appl. No.: 08/833,947

[22] Filed: Apr. 14, 1997

[51] Int. Cl.⁶ .............................. A61F 13/20; A61F 13/15
[52] U.S. Cl. ........................... 604/15; 604/904; 604/378; 604/383; 604/385.1
[58] Field of Search ..................... 604/904, 363, 604/383, 378, 385.1, 11–18; 602/62–65, 901

[56] References Cited

U.S. PATENT DOCUMENTS

| | | |
|---|---|---|
| 196,979 | 11/1877 | Kline ........................................ 604/904 |
| 1,884,089 | 10/1932 | Millner . |
| 2,146,985 | 2/1939 | Rabell . |
| 3,128,767 | 4/1964 | Nolan . |
| 3,340,874 | 9/1967 | Burgeni ..................... 604/904 |
| 3,766,921 | 10/1973 | Dulle . |
| 3,794,029 | 2/1974 | Dulle . |
| 3,857,395 | 12/1974 | Johnson et al. . |
| 3,986,511 | 10/1976 | Olofsson et al. . |
| 4,018,225 | 4/1977 | Elmi . |
| 4,185,631 | 1/1980 | McConnell . |
| 4,212,301 | 7/1980 | Johnson . |
| 4,393,871 | 7/1983 | Vorhauer et al. . |
| 4,838,882 | 6/1989 | Molinoff . |
| 5,231,992 | 8/1993 | Leon . |
| 5,514,085 | 7/1996 | Yoon . |
| 5,807,372 | 9/1998 | Balzar .................................. 604/385.1 |

*Primary Examiner*—John G. Weiss
*Assistant Examiner*—Dennis Ruhl
*Attorney, Agent, or Firm*—Matthew P. Fitzpatrick; Jeffrey V. Bamber; John M. Pollaro

[57] ABSTRACT

An absorbent article for absorption of bodily fluids is provided, including a layer of non-absorbent material defining a tunnel shaped loop and a central portion enclosed by the loop, and an absorbent material retained within the tunnel-shaped loop. The non-absorbent material includes a plurality of apertures through which fluid can flow to reach the absorbent material, and an overwrap material overlies the non-absorbent material to transport fluid over the surface of the non-absorbent material. Preferably the absorbent article is a tampon and the loop is ring shaped.

20 Claims, 4 Drawing Sheets

MULTI-LAYER ABSORBENT ARTICLE

BACKGROUND OF THE INVENTION

The present invention relates to articles for absorption of bodily fluids, e.g., menstrual tampons and articles for urine collection and absorption of wound exudate.

Many requirements are imposed on absorbent articles used to absorb bodily fluids. For example, it is often desired that such articles maintain substantially their original dimensions after absorption of fluid, that the fluid be retained by the device during movement of or pressure on the device, that the device not leak during use, and that the device be comfortable to the user.

In the case of menstrual tampons, tampons may be uncomfortable to remove if they swell excessively, should not leak during active use and should fit comfortably while also resisting leakage past the tampon.

SUMMARY OF THE INVENTION

The invention features improved absorbent articles, e.g., menstrual tampons. Absorbent articles made according to the invention resist swelling during use, with preferred articles maintaining substantially their initial dimensions after absorption of fluid during use. When used as tampons, the articles exhibit good resistance to leakage, substantially uniform surface wetting, and good resistance to exudation of fluid from the device during use.

In one aspect, the invention features an absorbent article including a resilient ring containing an absorbent material, and a central portion spanning the ring. The resilient ring is dimensioned to be positioned around a user's cervix, and, when the absorbent article is in position, the central portion is positioned below the user's cervix, e.g., to intercept menstrual fluid as it exits the cervix if the article is a tampon, and the resilient ring forms a gasket against the user's pericervical tissue to prevent leakage past the tampon. This positioning increases the likelihood that menstrual fluid will contact the article, by placing the article at the site of egress of the fluid. Moreover, because the absorbent material is contained within the ring, a wide variety of absorbent materials can be used, without the need for the absorbent material to have structural integrity or be suitable for contact with the vagina (requirements imposed on absorbent materials used in conventional tampons).

In another aspect, the invention features an absorbent article for absorption of bodily fluids, e.g., a tampon, including (a) a layer of non-absorbent material defining a tunnel shaped loop and a central portion enclosed by the loop (b) an absorbent material retained within the tunnel shaped loop (c) one or more apertures extending through said non-absorbent material, through which fluid can flow to reach the absorbent material; and (d) a wettable overwrap material overlying the non-absorbent material, constructed to transport fluid away from the site at which it contacts the overwrap material.

Preferably, the loop is a ring dimensioned to form a gasket between the cervix and the back wall of the vagina of a user of the tampon; more preferably, the ring has a diameter of from 1.5 to 2.5 inches. It is also preferred that the tampon be symmetrical about a plane that horizontally bisects that ring, and that the tampon be capable of functioning regardless of which side of the tampon, relative to this plane, is positioned closest to the user's cervix. This feature enables the tampon to be easily inserted, without requiring the user to determine which side should be positioned closest to the cervix.

Preferred embodiments may also include one or more of the following features: The tunnel is substantially oval in radial cross-section. The oval has a major axis of from 0.5 to 1.0 inches. The central portion is substantially flat. The central portion defines an opening that is covered by the overwrap material in a manner to prevent flow of fluid through the opening and to transport fluid contacting the portion of the overwrap covering the opening outward to the absorbent material. The non-absorbent material is substantially impermeable. The apertures are positioned at approximately 11 O'clock, 1 O'clock, 3 O'clock, 5 O'clock and 7 O'clock, viewing the ring as a clock face and defining the withdrawal cord as "6 O'clock". Alternatively, the apertures may be positioned to provide hinge points about which the loop and the enclosed central portion can be folded to collapse the absorbent article for insertion into a body cavity. The open space defined by the apertures is sufficient to enable fluid to flow into the absorbent material at a desired flow rate when the absorbent article is in use. The absorbent article includes from 1 to 1000 apertures. The non-absorbent material is an ethylene vinyl acetate foam. The non-absorbent material is perforated or is a discontinuous film. The absorbent material includes cotton, rayon, fluff pulp, and blends thereof. The absorbent material is a cotton/rayon blend. The absorbent material may include a superabsorbent material. The absorbent material includes a material that forms a gel upon contact with moisture, e.g., sodium carboxy methyl cellulose.

In another aspect, the invention features a menstrual tampon system including: (a) a tampon including a material defining a tunnel shaped loop and central portion, an absorbent material retained within the tunnel shaped loop a plurality of apertures extending through the non-absorbent material, through which fluid can flow to reach the absorbent material, and an overwrap material overlying the surface of the non-absorbent material to transport fluid over the surface of the non-absorbent material; and (b) an applicator for inserting the tampon into a body cavity, including: a holder tube constructed to hold the tampon prior to insertion, and a plunger tube, telescopically retained by the holder tube and constructed to, when inserted further into the holder tube, expel the tampon from the holder tube into the body cavity.

Preferred embodiments of this aspect of the invention include one or more of the following steps. The holder tube and the plunger tube are curved. The holder tube and the plunger tube define a radius of curvature of from about 2" to 8".

The invention also features methods of making an absorbent article, including (a) surrounding an absorbent material with a resilient, impermeable covering so that the covering defines a tunnel-shaped loop and the absorbent material is sealed within the tunnel, and (b) providing a web spanning the loop defined by the covering.

A preferred method includes (a) forming a first channel in a first portion of a formable material, the channel being constructed to define a closed loop, (b) providing a plurality of apertures in the formable material, in fluid communication with the channel, (c) placing an absorbent material in the channel, (d) forming a second channel, having dimensions substantially identical to those of the first channel, in a second portion of formable material, (e) aligning the first and second portions of formed material so that the corresponding channels in the first and second portions define a closed tunnel, (f) sealing the first and second portions together around the outer periphery of the closed loop, and (g) providing an overwrap material covering the outer surface of the tampon.

This aspect of the invention preferably includes one or more of the following features. The formable material includes a sheet of thermoplastic polymer and the forming steps comprise thermoforming the polymer. The formable material includes a moldable polymer and the forming steps comprise molding said polymer. The moldable polymer includes a curable material and the forming steps comprise introducing said curable material to a mold and allowing the curable material to cure. The curable material is a room temperature vulcanizable elastomer or a room temperature curable polymer. The first and second portions of formable material are sealed together by heat sealing. The method further includes laminating the overwrap to the formable material, preferably during or prior to the forming steps. The method further includes attaching a withdrawal cord to the absorbent material prior to placing the absorbent material in the channel.

In another aspect, the invention features an absorbent article comprising a generally annular, relatively inexpansible shell defining a generally annular cavity, an absorbent core disposed in the generally annular cavity, an entry passage for fluid to enter the generally annular shell and to be absorbed by the core, and a covering that provides passage of fluid over a surface of the relatively inexpansible shell.

The term "loop", as used herein, refers to any bent shape that encloses a central region; the loop need not be arcuate, but may have any desired shape, including but not limited to round, oval, triangular, square, rectangular, or trapezoidal. For most applications the loop is preferably "endless", i.e., defines a completely enclosed central region, to avoid leakage, but for some applications the loop could be interrupted, e.g., have a "horseshoe" shape.

Other features and advantages of the invention will be apparent from the Description of the Preferred Embodiment, drawings, and claims.

DESCRIPTION OF THE PREFERRED EMBODIMENTS

Figure 1:
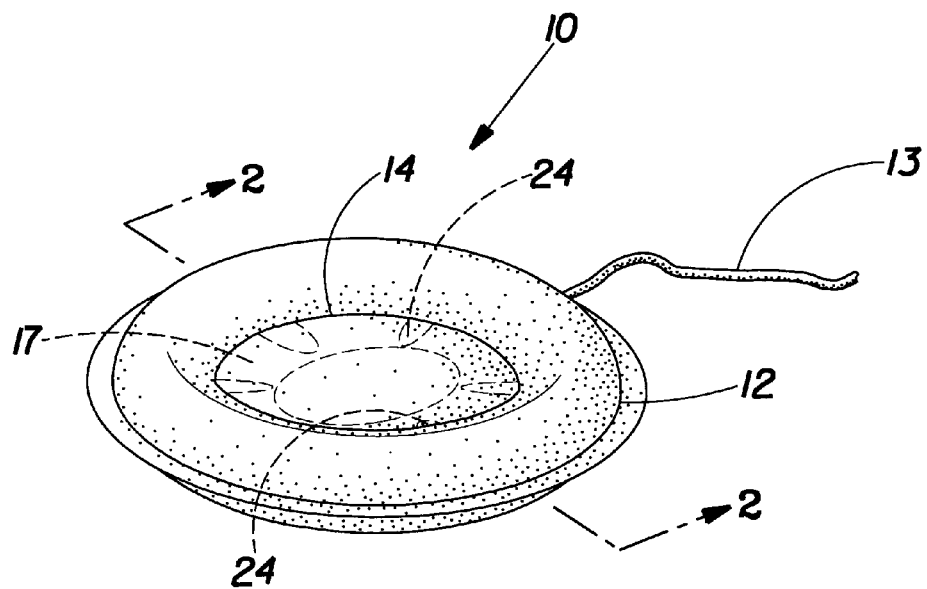
FIG. 1 is a perspective view of a tampon according to one embodiment of the invention, partially broken away to show the layers of the tampon and the ports in the non-absorbent layer.
Figure 2:
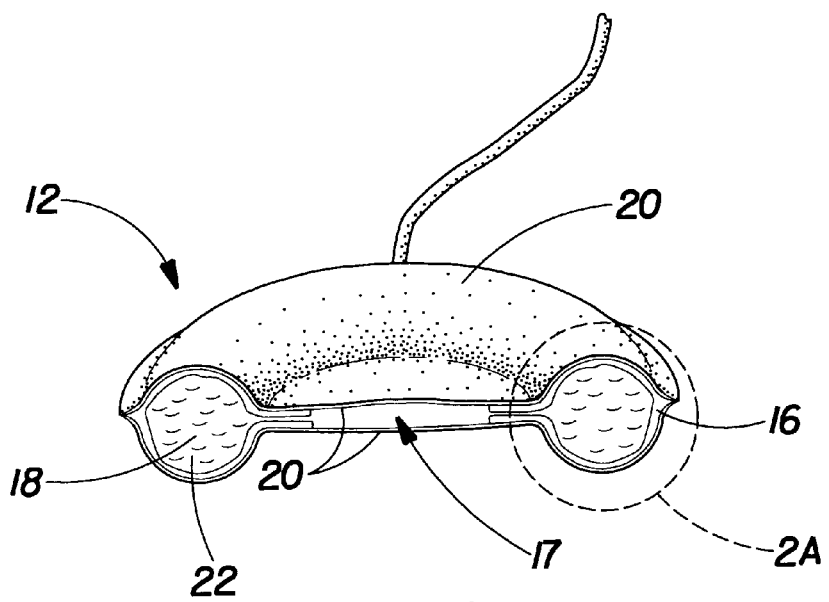
FIG. 2 is a partial perspective view of the tampon of FIG. 1, with a cross-section taken along line 2—2 of FIG. 1.
Figure 2A:
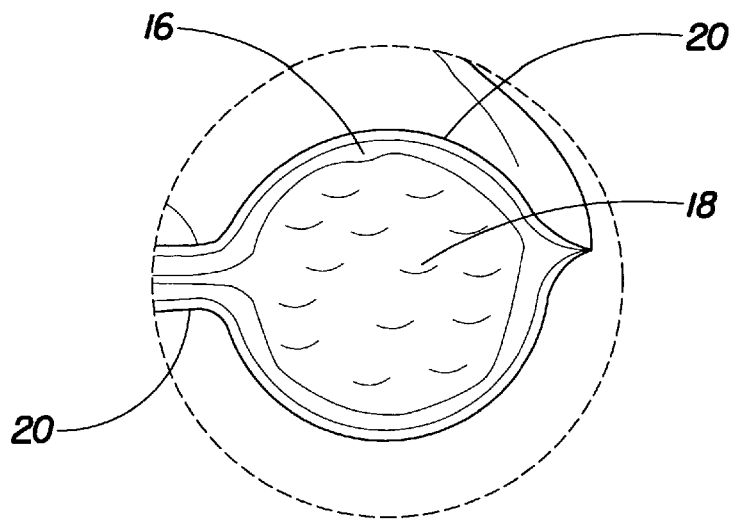
FIG. 2a is a highly enlarged, detail view of a portion of the tampon of FIG. 2.
Figure 3:
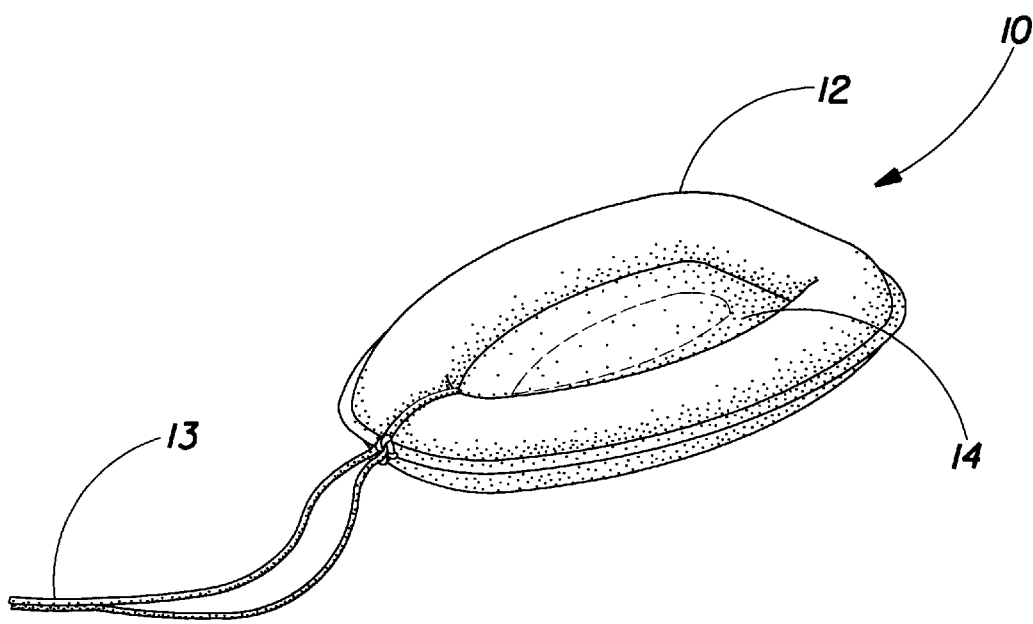
FIG. 3 is a perspective view of a tampon according to another embodiment of the invention.

Referring to FIGS. 1, 2 and 2a, tampon 10 is in the form of a ring 12 spanned by a central portion 14. As shown in FIG. 3, ring 12 is dimensioned to be positioned loosely around a user's cervix, and thus preferably has an inner diameter of from about 1.5 to 2.5 inches, most preferably about 2 inches. The central portion 14 is positioned below the cervix, and provides a reservoir for receiving menstrual fluid as it exits the cervix. The tampon 10 further includes a withdrawal cord 13, to enable the user to remove the tampon.

Referring to FIGS. 2 and 2a, the tampon 10 includes three layers: a non-absorbent layer 16, an absorbent core 18, and an overwrap layer 20. The non-absorbent layer 16 defines the ring 12 and a peripheral part of the central portion 14, and includes an opening 17 in the center of the central portion 14. This opening is covered by overwrap layer 20, which prevents flow of menstrual fluid through the opening 17. While opening 17 is not essential, it enables the tampon to be more easily folded for insertion. Absorbent core 18 is disposed within a tunnel 22 defined by ring 12. The non-absorbent layer 16 is preferably substantially fluid-impermeable, although it may be semi-permeable if desired. The relative impermeability of the non-absorbent material causes menstrual fluid to be transported over the surface of the tampon by the overwrap layer, as will be described further below, causing more uniform wetting of the tampon surface. Fluid is transported to the absorbent core, where it is retained, via ports 24 in the non-absorbent layer 16. The ports 24 are preferably positioned at approximately 11 O'clock, 1 O'clock, 3 O'clock, 5 O'clock, 7 O'clock and 9 O'clock, viewing the ring as a clock face and defining the position of the withdrawal cord as "6 O'clock", as shown in FIG. 1. Alternatively, if desired, the ports 24 can be positioned at opposite edges of the ring, to define an axis about which the tampon can be folded in half, so that they serve the additional function of providing hinge points to facilitate folding of the tampon prior to insertion and during withdrawal. The withdrawal cord is preferably attached to the tampon between the ports, at a location which enhances the hinge action of the ports when the cord is pulled during withdrawal.

The ports are also preferably placed on the inner perimeter of the ring 12 so that if fluid is exuded from the ports it will flow onto the central portion 14 where it can be reabsorbed without contacting vaginal tissue or leaking past the tampon. The total open area of the ports is preferably sufficient to enable flow of fluid into the tampon at a sufficient rate that fluid does not back up and leak past the tampon. Instead of ports, the non-absorbent material layer 16 can alternatively include a multitude of small perforations. If the ports provided are too few and/or too small, the rate of absorbency of the tampon in use may be reduced, while if the ports are too large, too many, or improperly placed the tampon may leak in use. The appropriate size and number of ports for a given tampon design can be readily determined by one skilled in the art, depending upon the other parameters of the tampon such as degree of absorptivity of the absorbent core.

Non-absorbent layer 16 is formed of a non-absorbent, resilient, formable sheet material. This layer defines the shape of the tampon, provides tunnel 22 which receives the absorbent core 18, and imparts resiliency to enable the tampon to be folded for insertion and to return to its ring shape after insertion.

Suitable sheet materials for layer 16 are those with sufficient resiliency and resistance to compression set to enable the tampon to unfold upon insertion. Preferred materials are relatively lightweight and/or of low density, to enable the tampon to stay in place in vivo, are biodegradable, are easily thermoformed at relatively low temperatures, and exhibit substantially no extension (do not stretch significantly under conditions of use). Preferably, the sheet material is a thermoplastic, to enable it to be thermoformed to the ring shape, and to enable the tampon to be manufactured in two halves which are heat-sealed together, as will be described further below. However, other types of resilient materials may be used if the tampon is manufactured without thermoforming, e.g., by molding the resilient material. Preferred sheet materials also resist swelling of the tampon during use, which provides advantageous dimensional stability. It is also preferred that the sheet material be a foam, for user comfort. One suitable foam is ethylene vinyl acetate foam, preferably having a density of from about 10 to 15 lbs/cu.ft. Closed cell polyurethanes are also suitable as foams. Other suitable materials include thermoplastic elastomers, e.g., styrene elastomers; silicone elastomers; latexes; synthetic rubbers; other thermoplastic sheet materials; and heat-vulcanizing or room-temperature vulcanizing (RTV) polymers, e.g., silicones; block copolymers, e.g., those commercially available under the tradename "KRATON", and blends of styrene elastomers with low density polyethylene.

The absorbent material absorbs and holds the menstrual fluid within the tampon. Virtually any absorbent material may be used. Preferred absorbent materials include natural fibers, e.g., cotton, synthetic fibers, e.g., rayon, fluff pulp, needle-punched engineered absorbents, fiber tows, tow webs, cellulosic sponge materials, and blends thereof. The absorbent material may include a superabsorbent material, and/or a material which forms a gel upon contact with moisture. For ease of manufacture, the absorbent material is preferably provided in an elongate cylindrical batt that is dimensioned to fit snugly within the tunnel 22. The amount of absorbent material used is selected to provide a desired absorbency, and impart a desired degree of "fullness" to the ring 12 for user comfort. The volume of the tunnel 22, and the amount and absorbency of the absorbent core 18, will determine the total absorbency of the tampon. Thus, these parameters can be varied as desired to design a tampon having a predetermined absorbency.

The overwrap material is provided to transport fluid over the surface of the tampon. Thus, suitable overwrap materials are those that are easily wetted by menstrual fluid, regardless of the angle of impingement of the menstrual fluid, and that readily transport menstrual fluid. Preferably, the overwrap has a soft feel for user comfort, does not retain a significant amount of fluid (enabling the fluid to be drawn into the absorbent material), is heat-sealable to the sheet material layer for ease of manufacturing, and has sufficiently small open space so that fluid does not leak through opening 17 but is instead transported to the absorbent material. Suitable overwrap materials include rayon, polypropylene, and rayon/polyethylene nonwovens, e.g., overwraps commercially available under the tradenames SONTARA and NOVONETTE.

As shown in FIG. 3, the absorbent article need not be ring-shaped, but can have other shapes, e.g., a "rowboat" shape as shown. Other suitable shapes include, but are not limited to, square, rectangular, oval, trapezoidal, and other shapes defining a closed loop. Preferably, the article has a shape which anchors it in a desired position, e.g., in a body cavity, and which blocks fluid flow past the absorbent article.

Figure 4:
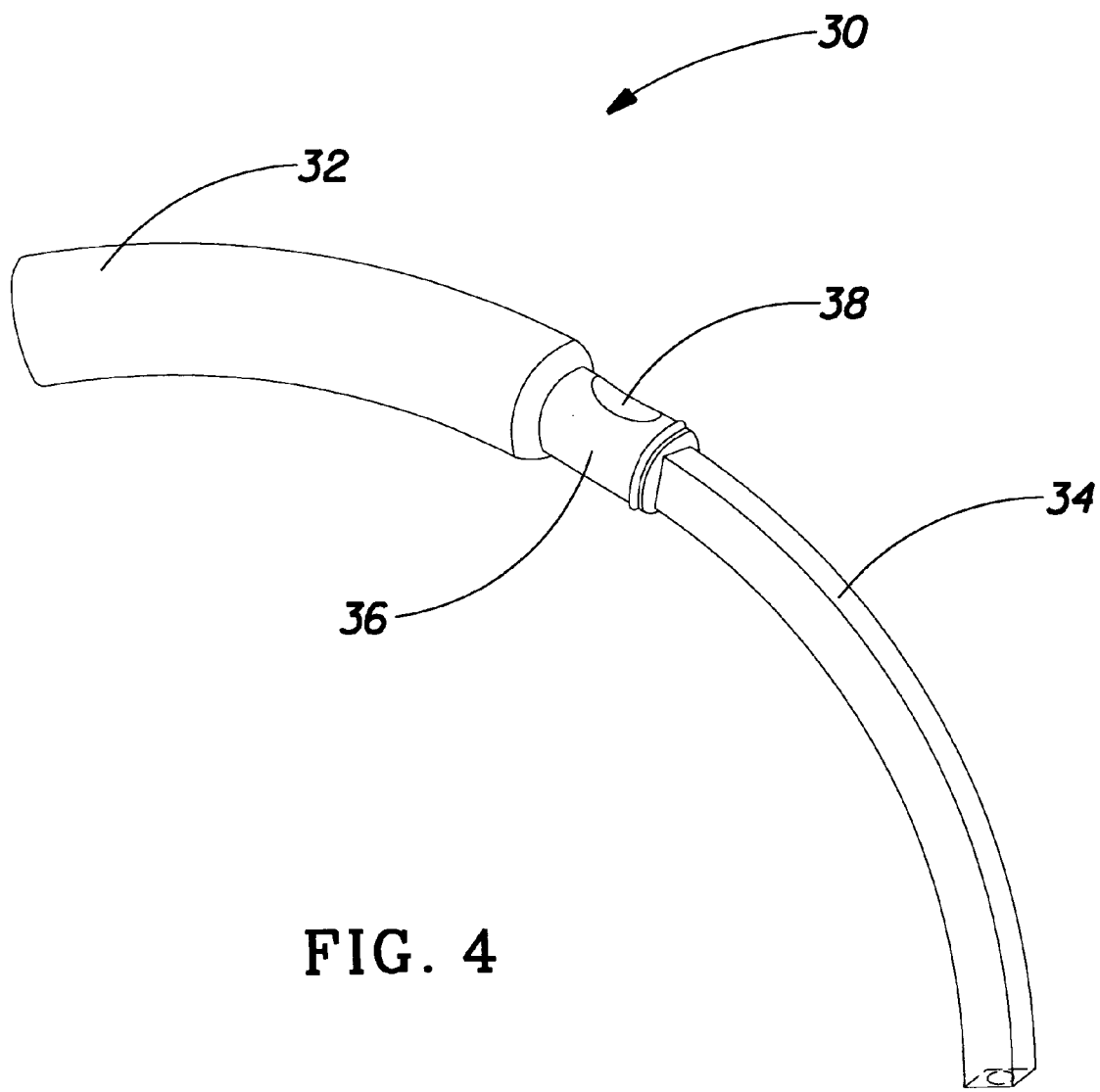
FIG. 4 is a perspective view of an applicator suitable for containing the tampon of FIG. 1.
Figure 5:
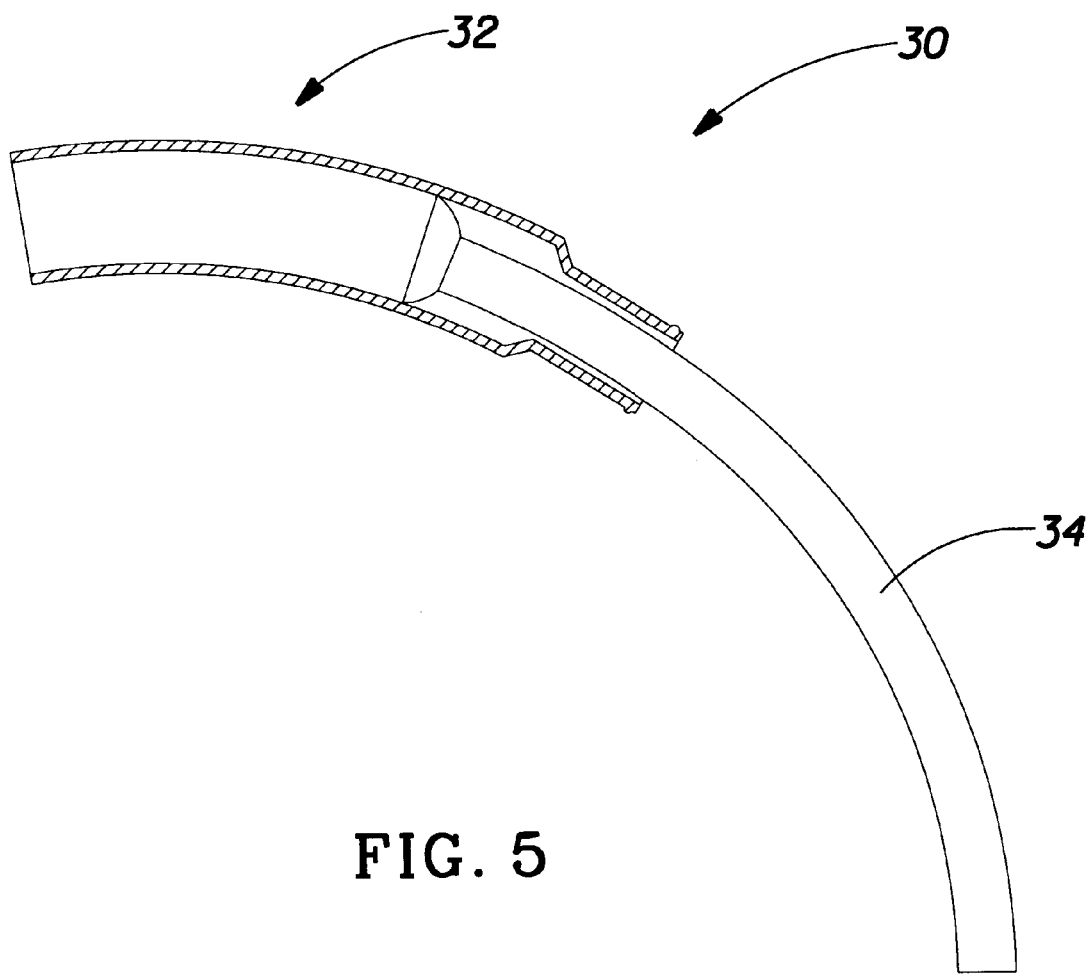
FIG. 5 is a cross-sectional side view of the applicator of FIG. 4, taken along line 5—5.

The tampon 10 can be inserted digitally, i.e., without the use of an applicator. Alternatively, the tampon can be inserted using a telescoping applicator, as is well known in the tampon field. A suitable applicator 30 is shown in FIGS. 4–5. The applicator 30 includes a holder tube 32, in which the tampon (not shown) is retained, and a plunger tube 34 which is constructed to be telescopically retained in a portion of the holder tube prior to insertion of the tampon, and to expel the tampon from the holder tube when the plunger tube is pushed further into the holder tube during insertion. If the materials used in the tampon have a tendency to heat- or compression-set when stored in a given position for a period of time, it is preferred that the tampon be provided to the user outside of the holder tube, and placed in the holder tube by the user prior to insertion. To facilitate this procedure, the holder tube is preferably open-ended, as shown.

For optimal placement of the tampon, it is preferred that either the tampon applicator 30 be curved, as shown, or the tampon itself have an arcuate profile when folded for insertion. Preferably, the applicator has a radius of curvature of from about 2" to 8", more preferably 3" to 5". The holder tube 32 preferably includes a finger-gripping portion 36, and a locating grip 38, e.g., a depression, as shown, or a protrusion. Locating grip 38 aids a user in properly orienting the curved applicator during insertion.

One suitable process for manufacturing the tampon 10 includes the following steps. First, a plurality of center openings are punched, and ports slitted, in a sheet of non-absorbent material. The center openings are spaced at suitable intervals so that each center opening is positioned at the center of a finished tampon when the sheet is cut into individual units.

Next, a sheet of heat-sealable overwrap material is placed adjacent the sheet of non-absorbent material, and the two layers are slit so that the sheet and overwrap can later be easily cut into individual units. Then, the two layers are thermoformed to create a channel that defines one half of a tunnel (dividing the tunnel approximately in half along the plane in which the central portion lies). The two layers are then preferably quenched to ambient temperature to set the form of the thermoformed sheet material.

The sheet is then cut into individual units, utilizing the previously made slits, each unit including a channel surrounding a central opening.

An absorbent batt is cut to length to fit into the channel, a withdrawal cord is looped around the absorbent batt, and the absorbent batt is pressed into the channel of a first one of the individual units. Then, a second individual unit, with an absorbent batt having been placed in its channel in the manner described above, is placed on top of, and in registration with, the first unit. The two units are then heat-sealed together around the outer periphery of the corresponding channels, forming a ring. The excess sheet material and overwrap is then trimmed from around the heat-sealed periphery, completing the manufacturing process. If desired, the first and second units can be hinged together, to aid in registration.

The tampon can be manufactured by any other suitable method. For example, the sheet material can be thermoformed, molded, or otherwise formed into the shape of a tire, i.e., into a ring having a C-shaped cross section and an open channel around its inner circumference. The absorbent material can then be inserted via this open channel, the edges of the channel sealed together to seal in the absorbent material, and the central web attached to the ring. Alternatively, the sheet material can be thermoformed, extruded, molded, or otherwise formed into an elongated tube, the tube can then be filled with absorbent material, bent into a ring or other loop shape, its edges sealed to seal in the absorbent material, and a central web joined to the inner periphery of the ring.

Other embodiments are within the claims. For example, while the invention has been described above in the context of tampons, the absorbent article may be any article for the collection of bodily fluids, e.g., a "donut" for the absorption of urine of immobilized patients, or an article for absorbing wound exudate. These articles are constructed in a similar manner, with adaptations to suit the different applications, as would be understood by one skilled in the art.

Additionally, while the tunnel 22 is illustrated as having a substantially oval radial cross-section, it may have any desired cross-section, e.g., circular or square, that defines an enclosed channel dimensioned to hold the absorbent core 18.

Moreover, although for simplicity of manufacturing and ease of insertion it is preferred that the absorbent article be constructed of two symmetrical halves, as described above, other manufacturing methods can be used, e.g., the tunnel can be formed from two channels having differing depths.

Further, while an applicator for inserting the absorbent article has been described above, the absorbent article can be constructed to be inserted in the vagina or in a desired body cavity by digital insertion or any other suitable means.

What is claimed is:

1. An absorbent article for absorption of bodily fluids comprising:
   (a) a layer of non-absorbent material defining a tunnel-shaped cavity loop and a central portion enclosed by the loop;
   (b) an absorbent material retained within said tunnel-shaped loop;
   (c) a plurality of apertures extending through said non-absorbent material, through which fluid can flow to contact said absorbent material; and
   (d) a wettable overwrap material overlying said layer of non-absorbent material, constructed to transport fluid over the surface of said non-absorbent material away from the site at which fluid contacts said overwrap material.

2. The absorbent article of claim 1 wherein the article is a tampon and the fluid is menstrual fluid.

3. The absorbent article of claim 1 wherein said non-absorbent material comprises a resilient polymeric material.

4. The absorbent article of claim 2 wherein said loop is a ring dimensioned to form a gasket between the cervix of a user of the tampon and the back wall of the vagina of said user.

5. The absorbent article of claim 4 wherein said ring has a diameter of from 1.5 to 2.5 inches.

6. The absorbent article of claim 4 wherein said tunnel-shaped loop is substantially oval in radial cross-section.

7. The absorbent article of claim 6 wherein said oval has a major axis of from 0.5 to 1.0 inches.

8. The absorbent article of claim 2 wherein said central portion is substantially flat.

9. The absorbent article of claim 2 where in said enclosed central portion defines an opening and said opening is covered by said overwrap material to transport fluid contacting the overwrap in the central portion outward to the absorbent material.

10. The absorbent article of claim 2 wherein said non-absorbent material is a resilient and substantially impermeable material.

11. The absorbent article of claim 2 wherein said apertures are positioned to provide hinge points about which said loop and said central portion can be folded to collapse said absorbent article for insertion into a body cavity.

12. The absorbent article of claim 2 further comprising a withdrawal cord attached to said loop portion of said absorbent article, wherein the apertures are positioned at approximately 11 O'clock, 1 O'clock, 3 O'clock, 5 O'clock and 7 O'clock, viewing the loop as a clock face and defining the withdrawal cord attachment location as "6 O'clock".

13. The absorbent article of claim 1 wherein said non-absorbent material is selected from the group consisting of: closed cell polyurethane foams, ethylene vinyl acetate foams, RTV rubbers, heat vulcanizable polymers, thermoplastic elastomers, latexes, synthetic rubbers, block copolymers, blends of styrene elastomers with low density polyethylene, silicone elastomers, and combinations thereof.

14. The absorbent article of claim 2 wherein said absorbent material is selected from the group consisting of natural fibers, synthetic fibers, fluff pulp, needle-punched engineered absorbents, fiber tows, tow webs, cellulosic sponge materials, superabsorbent materials, materials which forms a gel upon contact with moisture, and combinations thereof.

15. The absorbent article of claim 14 wherein said absorbent material comprises a cotton/rayon blend.

16. A menstrual tampon system comprising:
   (a) a tampon comprising:
      a layer of resilient material defining a tunnel shaped loop and a central portion enclosed by said loop;
      an absorbent material retained within said tunnel-shaped loop;
      a plurality of apertures extending through said resilient material through which fluid can flow to reach said absorbent material; and
      an overwrap material overlying said resilient material to transport fluid over the surface of said sheet material; and
   (b) an applicator for inserting said tampon into a body cavity, comprising:
      a holder tube constructed to hold said tampon prior to insertion, and
      a plunger tube, telescopically retained by said holder tube and constructed to, when inserted further into said holder tube, expel said tampon from said holder tube into said body cavity.

17. The system of claim 16 wherein said holder tube and said plunger tube are curved.

18. The system of claim 17 wherein said holder tube and said plunger tube define a radius of curvature of from about 4" to 6".

19. The system of claim 16 wherein said holder tube includes a finger-gripping portion, and said finger gripping portion includes a locating grip.

20. The system of claim 19 wherein said locating grip comprises a depression.

* * * * *